United States Patent [19]
Thys-Jacobs

[11] Patent Number: 6,034,075
[45] Date of Patent: Mar. 7, 2000

[54] METHOD OF TREATING POLYCYSTIC OVARIAN SYNDROME

[75] Inventor: Susan Thys-Jacobs, Larchmont, N.Y.

[73] Assignee: The Trustees of Columbia University in the City of New York, New York, N.Y.

[21] Appl. No.: 09/044,549

[22] Filed: Mar. 19, 1998

Related U.S. Application Data

[60] Provisional application No. 60/042,704, Mar. 20, 1997.

[51] Int. Cl.[7] .......................... A61K 31/59; A61K 33/42; A61K 33/10; A61K 33/06; A61K 33/00
[52] U.S. Cl. .......................... 514/168; 424/602; 424/677; 424/682; 424/686; 424/715; 424/722
[58] Field of Search .............................. 514/168; 424/602, 424/677, 682, 722, 715

[56] References Cited

U.S. PATENT DOCUMENTS

| | | | |
|---|---|---|---|
| 4,946,679 | 8/1990 | Thys-Jacobs | 424/682 |
| 5,354,743 | 10/1994 | Thys-Jacobs | 514/167 |

OTHER PUBLICATIONS

Channing CP, Hillensjo T, Schaef FW. Hormonal Control of Oocyte Meiosis, Ovulation and Luteinization in Mammals. Clin Endocrinol Metabol 1978;7:601–624. (Exhibit 4).

Davis JS, Weakland LL, Farese RV, West LA. Luteinizing Hormone Increases Inositol Triphosphate and Cytosolic Free Ca2+ in Isolated Bovine Luteal Cells. J Biol Chem 1987;262:8515–8521. (Exhibit 5).

Homa ST. Calcium and Meiotic Maturation of the Mammalian Oocyte. Mol Reprod Dev 1995;40:122–134. (Exhibit 6).

Jobin RM, Tomic M, Zheng L et al. Gonadotropin–Releasing Hormone–Induced Sensitization of Calcium–Dependent Exocytosis in Pituitary Gonadotrophs. Endocrinology 1995;136:3398–3405. (Exhibit 7).

Mattioli M, Barboni B, Seren E. Luteinizing Hormone Inhibits Potassium Outward Currents in Swine Granulosa Cells by Intracellular Calcium Mobilization. Endocrinology 1991;129:2740–2745. (Exhibit 8).

Powers RD, Paleos GA. Combined effects of calcium and dibutyryl cyclic AMP on germinal vesicle breakdown in the mouse oocyte. J Reprod Fert 1982:66:1–8. (Exhibit 9).

*Primary Examiner*—Theodore J. Criares
*Attorney, Agent, or Firm*—John P. White; Cooper & Dunham LLP

[57] ABSTRACT

The present invention is directed to a method of treating polycystic ovarian syndrome (PCO) with calcium alone, with vitamin D alone, or with the combination calcium and vitamin D. This invention further provides a method of treating infertility in a woman which comprises administering to the subject an amount of calcium or a derivative thereof effective to treat the infertility. The present invention is also directed to a method of treating irregular menses (oligo/amenorrhea), acne, or hirsutism, insulin resistance, or infertility which comprises administering a combination of calcium or a derivative thereof and vitamin D or a derivative thereof in an amount effective to treat irregular menses (oligo/amenorrhea), acne, or hirsutism, insulin resistance, or infertility. This invention also provides a method of preventing polycystic ovarian syndrome which comprises administering to the subject a combination of vitamin D or a derivative thereof and calcium or a derivative thereof in an amount effective to prevent the onset of polycystic ovarian syndrome.

21 Claims, No Drawings

METHOD OF TREATING POLYCYSTIC OVARIAN SYNDROME

This application claims the benefit of U.S. Provisional Application No. 60/042,704, filed Mar. 20, 1997, the content of which is incorporated into this application by reference.

Throughout this application, various publications are referenced by author and date. Full citations for these publications may be found listed alphabetically at the end of the specification immediately before the claims. The disclosures of these publications in their entireties are hereby incorporated by reference into this application in order to more fully describe the state of the art as known to those skilled therein.

BACKGROUND OF THE INVENTION

In 1935, Stein and Leventhal recognized the association of enlarged polycystic ovaries with amenorrhea, hirsutism and infertility. (Stein and Leventhal, 1935) Since then, the increased ovarian androgen production, hyperandrogenemia and menstrual irregularity have come to be known as polycystic ovary syndrome. (Rosenfeld, et al. 1972) Polycystic ovarian syndrome (PCO) has been described as one of the most common female endocrine disorders. Its incidence has been estimated to be about 5% in both adolescent and adult populations. (Declercq and van de Calseyde, 1977) It is characterized by hyperandrogenic chronic anovulation (increased androgen concentrations and cessation of ovulatory cycles), and clinically presents in the prepubertal period with any of the following: irregular menses, amenorrhea, dysfunctional uterine bleeding and hirsutism. (Frank, 1995) It is the most frequent cause of anovulation with approximately 55% of patients presenting with amenorrhea (absence of menses) and 70% with hirsutism. The syndrome comprises a spectrum of ovarian histological and morphological findings, ovarian steroid, gonadotropin and metabolic abnormalities.

The precise pathophysiologic mechanisms resulting in these endocrinologic disturbances is not known and is under intense debate. The most widely accepted theory is that PCO is a heterogenous disorder that increases intraovarian concentrations of androgens. (Barnes, and Rosenfeld, 1989) What is known, is that, there is a self perpetuating cycle of hormonal events resulting in polycystic ovaries, theca cell hyperplasia and arrested follicular cell development. (McKenna, 1988) Ovarian or adrenal androgens convert primarily to estrone in the periphery and feed back on the hypothalamic-pituitary axis to induce gonadotropin-releasing hormone (GnRH) synthesis with increased luteinizing hormone (LH) secretion and reduced follicular stimulating hormone (FHS) production. Increased LH secretion leads to hyperplasia of the ovarian stroma to produce more testosterone and androstenedione, inhibits production of sex hormone binding globulin and increases free androgen. This, then blocks follicular maturation leading to numerous follicles in various stages of development and eventually atresia. So, that a combination of hyperestronemia with hyperandrogenemia probably provides the hormonal milieu for PCO to occur. Evidence suggests that a dysregulation of the rate limiting enyme, cytochrome P450, resulting from elevations in luteinizing hormone, intrinsic defects of theca cell function or from hyperinsulinemia may then masculinize ovarian follicles causing follicular arrest accelerating atresia, and initiating the syndrome. (Rosenfeld, et al., 1990)

In recent years, PCO has been associated with a characteristic metabolic disturbance, insulin resistance and hyperinsulinemia. (Dunaif, et al., 1989) The hyperinsulinemia in PCO is not seen in all women but is more prevalent in obese young women. Evidence suggests that disordered insulin metabolism may precipitate increased androgen levels, while suppression of insulin levels with diazoxide or metformin can cause resumption of menses. Insulin stimulates androgen secretion in ovarian stroma in vitro and may act on the ovary via insulin growth factor receptors. (Barbieri, et al., 1986; Adashi, et al., 1985) The cellular mechanism underlying insulin resistance may reflect reduced binding of insulin to its receptor or a decreased expression of the insulin dependent glucose transporter protein GLT-4. (Jialal, et al.1987;Rosenbaum, et al., 1993) Treatment of PCO has traditionally been directed toward interrupting the self-perpetuating cycle of hormonal events. This has been done either with the use of surgery as in wedge resection of the ovary or through medical interventions by lowering LH levels (oral contraceptives and LHRH analogues). Other approaches have included enhancement of FSH secretion with clomiphene, human menopausal gonadotrophin or pulsatile LHRH therapy.

Over the past 20 years, numerous studies in invertebrates and vertebrates have established a role of calcium in oocyte maturation as well as in the resumption and progression of follicular development. Attention had originally centered on the significance of calcium during egg activation at fertilization by either sperm or the divalent ionophore A23187. Based on evidence that the calcium ionophore A23187 activated the eggs of vertebrates and marine invertebrates by mediating calcium fluxes, Steinhardt and colleagues proposed in 1974 that calcium may have a universal role in egg activation. (Steinhardt, et al. 1974) The maturation of the immature oocyte, and the activation and fertilization of the mature egg are two separate events in mammals. Evidence now exists that increases in intracellular calcium or calcium transients are clearly important at fertilization for invertebrates and vertebrates alike, and clearly important in the maturation of the non-mammalian oocytes. What is not clearly defined is the role of calcium in the meiotic maturation of the mammalian oocyte. The growth and maturation of the oocyte from primordial germ cell to oogonia to oocyte and then egg involves a series of mitotic and meiotic cell divisions. The transition from one meiotic phase to another is generally regulated at 3 control points and in many species, the control points are triggered by increases in intracellular calcium or by overriding meiotic arrest. (Lindner, et al., 1974) Primordial germ cells differentiate into oogonia with the final mitotic division in the fetal ovary to form a finite number of oocytes. At or following birth, the oocyte enters the dictyate stage (or G2 phase in mitotic cells) with an intact nuclear membrane termed the germinal vesicle. It is at this stage of oocyte development, that meiosis becomes arrested, and does not resume until puberty under the influence of LH. Under the influence of LH, the germinal vesicle breaks down and the oocyte enters M phase with resumption of meiosis and extrusion of the 1st polar body. Meiosis is then arrested again, awaiting the signal for fertilization. What is known is that: 1) denuded oocytes that are devoid of cumulus, spontaneously mature; 2) removal of the oocyte from its inhibitory environment or follicle results in spontaneous maturation, so that the oocyte is all set to go; 3) the immature oocyte, is generally accepted to be under the influence of the follicular environment or cumulus and is maintained in meiotic arrest; 4) increased cyclic AMP produced in the granulosa or cumulus oophorus cells helps to maintain meiotic arrest. What overrides meiotic arrest and stimulates meiotic resumption? LH is well established as the biological trigger in mammalian meiotic resumption. Luteinizing hormone is the physiological signal at puberty for oocyte maturation in both in vivo and in vitro studies. (Whitaker and Patel, 1990; Tsafriri, et al., 1972) Calcium is an important participant in the transduction of numerous signals in various tissues, and evidence suggests that LH release is calcium dependent via gonadotropin-releasing hormone induced sensitization of calcium dependent exocytosis. (Jobin, et al., 1995) Furthermore calcium is believed to be the primary intracellular signal in invertebrates and amphibians for the maturation of the oocyte and for initiation of development of the egg at fertilization. This hypothesis has been supported by three experimental models in different species: 1) an increase in calcium in the egg occurs at fertilization; 2) artificially raising intracellular calcium usually initiates egg development; 3) suppressing the natural rise in calcium prevents the initiation of egg development. LH stimulates rapid increases in intracellular calcium in both cow luteal and pig granulosa cells. (Channing, et al., 1978; Davis, et al., 1987; Mattioli, et al., 1991) These LH mediated calcium oscillations are characterized by an initial transient through intracellular calcium mobilization followed by a second wave resulting from calcium influx from the extracellular environment. Manipulation of extracellular calcium such as high concentrations of calcium can override meiotic arrest in mouse oocytes whereas reduced calcium concentrations can inhibit meiotic resumption of follicle-enclosed rat oocytes following LH stimulation. (Powers and Paleos, 1982) In other words, increases or changes in intracellular calcium are required for the oocyte to mature or progress to the next stage. In mammals, a series of calcium transients occur at fertilization and appear to be required for release of the second metaphase arrest, but a role for calcium in triggering meiotic resumption and progression in mammalian oocyte is still not clearly defined, though it is strongly suspected. (Homa, 1995) Similarly, the role of vitamin D in oocyte maturation has not been defined. Nor has a role for calcium and vitamin D in PCO, hirsutism, acne development and fertility been defined.

What triggers this vicious hormonal cycle with altered feedback loops resulting in arrested follicular development and the clinical entity of PCO, to date, has not been fully explained. Primary abnormalities of the ovary, adrenal and pituitary have been proposed and much debate has focused on whether it is even one disorder or multiple. It is proposed, here, that calcium dysregulation inhibits normal follicular development resulting in infertility, oligo/amenorrhea, acne formation and hirsutism. This invention establishes an essential role of calcium regulation in the polycystic ovarian syndrome in that correction of the calcium abnormalities with calcium, vitamin D or calcium and vitamin D can either reverse or improve symptoms of the syndrome.

SUMMARY OF THE INVENTION

This invention provides a method of treating a subject afflicted with polycystic ovarian syndrome which comprises administering to the subject an amount of calcium or a derivative thereof, or an amount of vitamin D or a derivative thereof or a combination of vitamin D or a derivative thereof and calcium or a derivative thereof effective to treat the polycystic ovarian syndrome.

This invention further provides a method for treating irregular menses (oligo/amenorrhea), acne, or hirsutism, insulin resistance, or infertility which comprises administering to a subject having symptoms associated with acne, hirsutism, insulin resistance or infertility an amount of calcium or a derivative thereof, or vitamin D or a derivative thereof or, a combination of calcium or a derivative thereof and vitamin D or a derivative thereof effective to treat the above-described symptoms.

This invention further provides a method of preventing polycystic ovarian syndrome in a subject afflicted with irregular menses (oligo/amenorrhea), acne, or hirsutism, insulin resistance, infertility or abnormal ovarian morphology which comprises administering to the subject an amount of vitamin D or a derivative thereof, or calcium or a derivative thereof, or a combination of calcium or a derivative thereof and vitamin D or a derivative thereof effective to prevent the onset of polycystic ovarian syndrome.

This invention method of treating infertility in a female which comprises administering to the subject an amount of calcium or derivative thereof, or vitamin D or a derivative thereof, or a combination of vitamin D or a derivative thereof and calcium or a derivative thereof effective to treat the infertility.

DETAILED DESCRIPTION OF THE INVENTION

This invention provides a method of treating a subject afflicted with polycystic ovarian syndrome which comprises administering to the subject an amount of calcium or a derivative thereof effective to treat the polycystic ovarian syndrome.

This invention further provides a method of treating a subject afflicted with polycystic ovarian syndrome which comprises administering to the subject an amount of vitamin D or a derivative thereof effective to treat the polycystic ovarian syndrome.

Another embodiment of this invention is a method of treating a subject afflicted with polycystic ovarian syndrome which comprises administering to the subject a combination of calcium or a derivative thereof and vitamin D or a derivative thereof in an amount effective to treat the polycystic ovarian syndrome.

Polycystic ovarian syndrome has been characterized by symptoms such as hyperandrogenic chronic anovulation (increased androgen concentrations and absence of ovulatory cycles. In the prepubertal period, the subjects afflicted with the syndrome exhibit symptoms such as irregular menses, amenorrhea, dysfunctional uterine bleeding and hirsutism, alone or in combination.

This invention also provides a method of treating infertility in a female which comprises administering to the subject a combination of vitamin D or a derivative thereof and calcium or a derivative thereof in an amount effective to treat the infertility.

This invention further provides a method of treating infertility in a female which comprises administering to the subject an amount of vitamin D or a derivative thereof effective to treat the infertility.

This invention also provides a method of treating infertility in a female which comprises administering to the subject an amount of calcium or a derivative thereof effective to treat the infertility.

As describe herein, the term "female" includes, but is not limited to, human or other mammals.

The infertility described herein may, but not exclusively, be caused by polycystic ovarian syndrome.

As used herein, "vitamin D derivative" comprises a group consisting of, but not limited to, ergocalciferol (D2), cholecalciferol (D3), calcidiol (25 hydroxyvitamin D), or calcitriol (1,25 dihydroxyvitamin D).

As used herein, "calcium derivative" comprises elemental calcium in different forms, such as, but not limited to, calcium carbonate, calcium citrate, calcium gluconate, calcium lactate, calcium acetate, or calcium stearate.

Depending on the mode of administration, calcium treatment can vary. For example, oral administration of calcium can range from about 500 to about 3000 mg per day. A specific embodiment of the invention is wherein the calcium is calcium carbonate and the amount is from about 300 mg to about 400 mg and is administered orally two–six times per day. One skilled in the art could determine which dose and mode of administration would be most appropriate for the subject.

Depending on the mode of administration, vitamin D treatment can vary. For example, an embodiment of the subject invention is where the vitamin D derivative is vitamin D2 or D3 and is administered orally at 400 to about 5000 IU per day. In another embodiment, the vitamin D derivative is vitamin D2 or D3 and is administered orally in an amount from about 50,000 to about 300,000 IU per week. In another embodiment of the subject method, the vitamin D derivative is vitamin D2 and is administered intramuscularly in an oil base in an amount from 100,00 to about 500,000 IU once every 2–3 months. In another specific embodiment of the subject method, the vitamin D derivative is calcitriol and is administered orally in an amount from about 0.25 to 1.00 mg per day. One skilled in the art could determine which dose and mode of administration would be most appropriate for the subject.

Administration of calcium or a derivative thereof, or vitamin D or a derivative thereof, or a combination of calcium or a derivative thereof and vitamin D or a derivative thereof can be effected or performed using any of the various methods known to those skilled in the art. The administering comprises administering intravenously, intramuscularly, subcutaneously, orally, sublingually, parenterally, or transdermally.

When administered in combination, the amounts of the calcium or derivative thereof, and the vitamin D or derivative thereof will vary depending on the mode of administration. For example, in one embodiment, the calcium or the derivative thereof is in an amount of about 1500 mg per day and the vitamin D or the derivative thereof is in an amount of about 2000 IU per day.

In another embodiment, the calcium or the derivative thereof is in an amount of about 1500 mg per day and the vitamin D or the derivative thereof is in an amount of about 3000 IU per day.

In a further embodiment, the calcium or the derivative thereof is in an amount of about 1000 mg per day and the vitamin D or the derivative thereof is in an amount of about 2000 IU per day.

In another embodiment, the calcium or the derivative thereof is in an amount of about 1000 mg per day and the vitamin D and the derivative thereof is in an amount of about 1000 IU per day.

In a further embodiment, the calcium or the derivative thereof is in an amount of about 500 mg and the vitamin D or the derivative thereof is in an amount of 800 IU. In a specific embodiment, the calcium or the derivative thereof can be administered two or three times per day.

The calcium or the derivative thereof and vitamin D or the derivative thereof are administered in various forms, including, but not limited to, a tablet, capsule, powder, liquid, candy, cookie, or transdermal patch. Methods of administering the above-described substances are well-known in the art.

This invention further provides for a method of treating irregular menses (oligo/amenorrhea), acne, or hirsutism, insulin resistance, or infertility which comprises administering to a subject having symptoms associated with acne, hirsutism, insulin resistance or infertility a combination of calcium or a derivative thereof and vitamin D or a derivative thereof in an amount effective to treat irregular menses (oligo/amenorrhea), acne, or hirsutism, insulin resistance, or infertility.

This invention also provides a method of treating irregular menses (oligo/amenorrhea), acne, or hirsutism, insulin resistance, or infertility which comprises administering to a subject having symptoms associated with acne, hirsutism, insulin resistance or infertility an amount of calcium or a derivative thereof effective to treat irregular menses (oligo/amenorrhea), acne, or hirsutism, insulin resistance, or infertility.

This invention also provides a method for treating irregular menses (oligo/amenorrhea), acne, or hirsutism, insulin resistance, or infertility which comprises administering to a subject having symptoms associated with acne, hirsutism, insulin resistance or infertility an amount of vitamin D or a derivative thereof effective to treat the irregular menses (oligo/amenorrhea), acne, or hirsutism insulin resistance, or infertility.

As used herein, "vitamin D derivative" comprises a group consisting of, but not limited to, ergocalciferol (D2), cholecalciferol (D3), calcidiol (25 hydroxyvitamin D), or calcitriol (1,25 dihydroxyvitamin D).

As used herein, "calcium derivative" comprises elemental calcium in different forms, such as, but not limited to, calcium carbonate, calcium citrate, calcium gluconate, calcium lactate, calcium acetate, or calcium stearate.

Administration of calcium or a derivative thereof, or vitamin D or a derivative thereof, or a combination of calcium or a derivative thereof and vitamin D or a derivative thereof can be effected or performed using any of the various methods known to those skilled in the art. The administering comprises administering intravenously, intramuscularly, subcutaneously, orally, sublingually, parenterally, or transdermally.

This invention further provides a method of preventing polycystic ovarian syndrome in a subject afflicted with irregular menses (oligo/amenorrhea), acne, or hirsutism, insulin resistance, infertility or abnormal ovarian morphology which comprises administering to the subject an amount of vitamin D or a derivative thereof effective to prevent the onset of polycystic ovarian syndrome.

This invention also provides a method of preventing polycystic ovarian syndrome in a subject afflicted with irregular menses (oligo/amenorrhea), acne, or hirsutism, insulin resistance, infertility or abnormal ovarian morphology which comprises administering to the subject an amount of calcium or a derivative thereof effective to prevent the onset of polycystic ovarian syndrome.

This invention also provides a method of preventing polycystic ovarian syndrome in a subject afflicted with irregular menses (oligo/amenorrhea), acne, or hirsutism, insulin resistance, infertility or abnormal ovarian morphology which comprises administering to the subject a combination of vitamin D or a derivative thereof and calcium or a derivative thereof in an amount effective to prevent the onset of polycystic ovarian syndrome.

As used herein, "vitamin D derivative" comprises a group consisting of, but not limited to, ergocalciferol (D2), cholecalciferol (D3), calcidiol (25 hydroxyvitamin D), or calcitriol (1,25 dihydroxyvitamin D).

As used herein, "calcium derivative" comprises elemental calcium in different forms, such as, but not limited to, calcium carbonate, calcium citrate, calcium gluconate, calcium lactate, calcium acetate, or calcium stearate.

Administration of calcium or a derivative thereof, or vitamin D or a derivative thereof, or a combination of calcium or a derivative thereof and vitamin D or a derivative thereof can be effected or performed using any of the various methods known to those skilled in the art. The administering comprises administering intravenously, intramuscularly, subcutaneously, orally, sublingually, parenterally, or transdermally.

This invention is illustrated in the Experimental Details section which follows. This section is set forth to aid in an understanding of the invention but is not intended to, and should not be construed to, limit in any way the invention as set forth in the claims which follow thereafter. cl Experimental Details First Series of Experiments The intent of this investigation was 1) to understand the extent to which calcium metabolism was disturbed in polycystic ovarian syndrome, 2) to characterize the pattern of calciotropic hormone involvement in polycystic ovary syndrome, 3) to determine whether correction of the calcium dysregulation resulted in normalization of the biochemical markers of PCO and, 4) to determine whether calcium and vitamin D therapy was effective in activating follicular development, resumption of menses and improvement of hirsutism and acne.

METHODS

Selection

Premenopausal women between the ages of 18 and 50 years were selected if they met the 1990 NIH Consensus criteria of polycystic ovarian syndrome (Zawadski and Dunaif):

The following constitutes the selection criteria:

a) chronic oligomenorrhea/anovulation—oligomenorrhea defined as menstrual cycle>35 days and or scanty menstrual flow;

b) hyperandrogenism—signs include hirsutism, acne, alopecia; signs of androgen excess must be present even in the absence of elevated serum androgen levels; androgen production rates are invariably elevated; elevation of at least one peripheral androgen is usually present, but single determinations can miss significant androgen excess; testosterone may be normal due to depression of SHBG and free testosterone may be more helpful; androstenedione is commonly elevated; dehydroepiandrosterone(s) (DHEA) or (DHEAS) may be elevated; 17 hydroxyprogesterone (170HP) may be increased slightly;

c) abnormal ovarian morphology as reflected on ultrasound—may be present; enlarged ovaries with multiple small peripheral or subcapsular cysts and an increased amount of stroma; true virilization is uncommon; usually both ovaries are involved but unilateral enlargement has been reported;

d) abnormal gonadotropins—increased mean LH, normal to low FSH levels; the ratio of LH>FSH is 2.4;

e) abnormal insulin regulation—acanthosis nigricans may be present.

Exclusion criteria

Women were excluded from the clinical trial for the following reasons: ovarian androgen secreting tumors, adrenal androgen secreting tumors, Cushing's syndrome, classical or late onset congenital adrenal hyperplasia, hyperprolactinemia, primary hyperparathyroidism, malignancy, gastrectomy, inflammatory bowel disease, the use of anticonvulsants, renal failure, mental retardation.

The study's design was an observational trial.

Measurements

Clinical evaluation involved a detailed medical, menstrual history and physical examination. Routine baseline chemistries and a complete blood count were obtained in all patients.

Calciotropic hormones were obtained initially and repeated following treatment.

Determinations of prolactin (PRL), DHEA, 170HP, androstenedione, AM cortisol following a 1 mg decadron suppression test, total and free testosterone, LH, FSH were obtained during the initial visit. Determinations of total calcium, intact parathyroid hormone (PTH), 25 hydroxyvitamin D (25OHD), 1,25 dihydroxyvitamin D $(1,25(OH)_2D)$ were obtained in all patients.

Pelvic ultrasound was obtained in all patients.

At each visit, the women were questioned about interim medical history including menses, drug compliance, adverse effects.

In order to prevent endometrial hyperplasia, progesterone in the form of Provera was provided every 3 months if not already prescribed to induce menses. Women who were already taking oral contraceptives as treatment for PCO were maintained on these medications.

Specialized laboratory tests were conducted. While the calcium regulating hormones included 25OHD, $1,25(OH)_2D$, were tested at Corning-Nichols Institute, the remaining blood assays were performed in the Endocrine and Chemistry Laboratories at Columbia Presbyterian Medical Center. The following lists the assays conducted:

(1) PTH levels: PTH was assayed with a chemiluminescent method that detects only the intact form of the molecule. Intra-assay and interassay variations are 3.4% and 5.6% respectively. The normal range for this assay is 10–65 pg/ml. (Nussbaum, et al., 1987);

(2) 25OHD assay: After extraction of serum samples, 25OHD was measured in a radio-binding assay. The intra-assay and interassay variations for this assay are 7.5% and 9.6% respectively. The normal range is 9–52 ng/ml. (Adams, et al., 1981); and (3) $1,25(OH)_2D$ assay: This vitamin D metabolite was assayed in a radioreceptor assay. The normal range is 15–60 pg/ml. The intra-assay and interassay variations for this assay are 7.6% and 9.8% respectively. (Reinhard, et al., 1984).

Results: (see Table 1)

Eight premenopausal women with documented chronic anovulation and hyperandrogenism were evaluated. Ages ranged from 23 to 41 years (31±7.7). Six had abnormal pelvic sonograms with multiple ovarian follicular cysts. Three were amenorrheic and required the use of progesterone every 3 months to induce menses. Three had oligomenorrhea of which one had been prescribed oral contraceptives for regularization of menses. Two had regular menstrual cycles. All had normal decadron suppression tests, prolactin, and 17 hydroxyprogesterone levels. Three had evidence of acanthosis nigricans (insulin resistance). All had evidence of hirsutism; one had alopecia. All had 25OHD≦20 ng/ml (9.0±5.4 ng/ml, nl:9–52) (Of note, most authorities cite that 25OHD concentrations less than 20 ng/ml represent vitamin D insufficiency). The mean PTH was 49±14 pg/ml (nl:10–65 pg/ml) with elevated PTH levels in 4 women (Of note, in premenopausal women, the upper limit of normal for a PTH level is 50 pg/ml). One had a 1,25(OH)2D<5 pg/ml (nl:15–60). All were normocalcemic (9.1±0.4 mg/dl). Calcium was prescribed as 1500 to 2000 mg of elemental calcium per day in the form of calcium carbonate. Vitamin D in the form of ergocalciferol was prescribed in the dose of 50,000 IU per day for 7 days and then, 50,000 IU weekly. Vitamin D repletion and calcium supplementation resulted in normal menstrual cycles within 2 months for three patients, while two became pregnant. The 25OHD concentrations were maintained with therapy at or above 30–40 ng/ml. The other 3 patients maintained normal menstrual cycles. The profound vitamin D deficiency and calcium dysregulation in these women may have been responsible for the arrested follicular development.

This is the first study that has explored the relationship between PCO and calcium metabolism and found that calcium and vitamin D therapy resulted in resumption of menses, normalization of menstrual cycles, fertility, improvement of acne, hirsutism and alopecia.

Based on the eight premenopausal women tested with documented PCO and profound vitamin D deficiency, it is proposed that the calcium dysregulation and/or vitamin D deficiency in these women is/are responsible for arrested follicular development, hirsutism, acne and the menstrual irregularities while correction of the calcium abnormalities restores fertility, improves the acne, hirsutism, and insulin resistance.

had normal decadron suppression tests, prolactin, and 17-hydroxyprogesterone levels. The mean 25 hydroxyvitamin D level was 11.2±6.9 ng/ml (nl:9–52). The mean intact parathyroid hormone level was 47±19 pg/ml (nl:10–65 pg/ml). One had a 1,2S dihydroxyvitamin D <5 pg/ml (nl:15–60). All were normocalcemic (9.3±0.4 mg/dl). Vitamin D repletion and calcium supplementation resulted in normal menstrual cycles within 2 months for seven patients, while 2 became pregnant. The other 4 patients maintained normal menstrual cycles.

In conclusion, vitamin D and calcium therapy resulted in a resumption of normal menses in women with PCO. We propose that calcium and vitamin D may be important in normal reproductive and menstrual function, and that vitamin D deficiency and calcium dysregulation may be responsible, in part, for oligo-amenorrhea.

REFERENCES

1. Stein I F, Leventhal M L. Amenorrhea associated with bilateral polycystic ovaries. Am J Obstet Gynecol 1935;29:181
2. Rosenfeld R L, Ehrlich E N, Cleary R E. Adrenal and ovarian contributions to the elevated free plasma androgens in hirsute women. J Clin Endocrinol Metab 1972;34:92–8.
3. Declercq J A, van de Calseyde J F. Polycystic ovarian disease: diagnosis, frequency and symptoms in a general

TABLE 1

| Patient | Age | 25OHD | 1,25OH2D | iPTH | T. Cal | T. Test | PRL | DHEA | 17OHP |
|---|---|---|---|---|---|---|---|---|---|
| 1 | 40 | 4 | 59 | 73 | 9.1 | 142 | 11.0 | 258 | 48 |
| 2 | 23 | 6 | 35 | 54 | 9.7 | 47 | 6.7 | 405 | 91 |
| 3 | 24 | 10 | <5 | 27 | 8.8 | 54 | 5.7 | 301 | 69.7 |
| 4 | 38 | 9 | 41 | 55 | 8.9 | 38 | 5.1 | 99 | 69.1 |
| 5 | 24 | 8 | 53 | 47 | 9.6 | 96 | 11.5 | 36 | 55 |
| 6 | 32 | <5 | 33 | 47 | 8.9 | 19 | 9.5 | 200 | 294 |
| 7 | 26 | 19 | 43 | 32 | 8.7 | 47 | 7.9 | 384 | 289 |
| 8 | 41 | 11 | 46 | 56 | 9.2 | 69 | 8.3 | 239 | 281 |
| Mean | 31 ± 7.7 | 9 ± 5.4 | 39 ± 18 | 49 ± 14 | 9.1 ± 0.4 | 64 ± 39 | 8.2 ± 2 | 240 ± 128 | 150 ± 116 |
| Normal | | 9–52 ng/ml | 15–60 pg/ml | 10–65 pg/ml | 8.4–10.2 mg/dl | 20–80 ng/dl | 1–25 ng/dl | 45–270 mcg/dl | 40–300 ng/dl |

Abbreviations: 25OHD = 25 hydroxyvitamin D; 1,25(OH)$_2$D = 1, 25 dihydroxyvitamin D; iPTH = intact parathyroid hormone; T. Cal = calcium levels; T. Test = testosterone; PRL = prolactin; DHEA = dehydroepiandrosterone; 17OHP = 17 hydroxyprogesterone.

Second Series of Experiments

Numerous studies in invertebrates and vertebrates have established a role of calcium in oocyte maturation as well as in the resumption and progression of follicular development. Polycystic ovarian syndrome (PCO) is characterized by hyperandrogenic chronic anovulation, theca cell hyperplasia and arrested follicular cell development. We now report our cumulative experience in thirteen women with polycystic ovarian syndrome (PCO) with evidence of calcium dysregulation and vitamin D deficiency. We propose that the calcium dysregulation may have inhibited normal follicular development in this syndrome.

Thirteen premenopausal women with documented chronic anovulation and hyperandrogenism were evaluated. Ages ranged from 21 to 41 years (31±7.9). Nine had abnormal pelvic sonograms with multiple ovarian follicular cysts. Four were amenorrheic and required the use of progesterone every 3 months to induce menses, Nine had a history of oligomenorrhea of whom four had regular menses due to pregnancy or prescribed oral contraceptives. Two had dysfunctional bleeding. All had evidence of hirsutism and 2 had alopecia. Five had evidence of acanthosis nigricans. All gynaecological practice. Br J Obstet Gynaecol 1977;84:380–5.
4. Franks S. Polycystic Ovary Syndrome. N Engl J Med 1995;13:853–861.
5. Barnes R, Rosenfield R L. The polycystic ovary syndrome: pathogenesis and treatment. Ann Int Med 1989;110:386–399.
6. McKenna T J. Current concepts: Pathogenesis and Treatment of polycystic ovary syndrome. N Engl J Med 1988; 9:558–562.
7. Rosenfield R L, Barnes R B, Cara J F, Lucky A W. Dysregulation of cytochrome P450c 17 alpha as the acute cause of polycystic ovary syndrome, Fertil Steril 1990;53:785–91.
8. Dunaif A, Segal K R, Futterweit W, Dobrjansky A. profound peripheral insulin resistance, independent of obesity in the polycystic ovary syndrome. Diabetes 1989;38:1165.
9. Barbieri R L, Makris A, Randall R W, et al. Insulin stimulates androgen accumulation in incubations of ovarian stroma obtained from women with hyperandrogenism. J Clin Endocrinol Metab 1986;62:904–910.

10. Adashi E Y, Resnick C E, D'Ercole A J, et al. Insulin growth factors as intraovarian regulators of granulosa cell growth and function. Endocr Rev 1985;6:400–420.
11. Jialal I, Naiker P, Reddi K, Moodley J, Joubert S M. Evidence for insulin resistance in nonobese patients with polycystic ovarian disease. J Clin Endocrinol Metab 1987;64:1066–69.
12. Rosenbaum D, Haber R S, Dunaif A. Insulin resistance in polycystic ovary syndrome: decreased expression of GLUT-4 glucose transporters in adipocytes. Am J Physiol 1993;264:E197–E202.
13. Steinhardt R, Epel D, Carroll E, and Yanagimachi R. Calcium ionophore: a universal activator for unfertilized eggs? Nature 1974;252:41–43.
14. Whitaker M, Patel R. Calcium and cell cycle control. Development 1990; 108:525–542.
15. Lindner H R, Tsafriri A, Lieberman M E, et al. Recent Prog Hormone Res 1974;30:79–138.
16. Tsafriri A, Lindner H R, Zor U. J Reprod Fertil 1972;31:39–50.
17. Jobin R M, Tomic M, Zheng L et al. Gonadotropin releasing hormone induce sensitization of calcium dependent exocytosis in pituitary gonadotrophs. Endocrinology 1995;136:3398–3405.
18. Channing C P, Hillensjo T, Schaef F W. Hormonal control of oocyte meiosis, ovulation and luteinization in mammals. Clin Endocrinol Metabol 1978;7:601–624.
19. Davis J S, Weakland L L, Farese R V, West L A. Luteinizing hormone increases inosital triphosphate and cytosolic free Ca2+ in isolated bovine luteal cells. J Biol Chem 1987;262:8515–8521.
20. Mattioli M, Barboni B, Seren E. Luteinizing hormone inhibits potassium outward currents in swine granulosa cells by intracellular calcium mobilization. Endocrinology 1991;129:2740–2745.
21. Powers R D, Paleos G A. Combined effects of calcium and dibutyryl cyclic AMP on germinal vesicle breakdown in the mouse oocyte. J Reprod Fert 1982:66:1–8.
22. Homa S T. Calcium and meiotic maturation of the mammalian oocyte. Mol Reprod Dev 1995;40:122–134.
23. Zawadski J K, Dunaif A. Diagnostic criteria for polycystic ovary syndrome: towards a rational approach. In: Current Issues in Endocrinology and Metabolism: Polycystic Ovary Syndrome. Dunaif A, Givens J, Haseltine F P, Merriam G H (eds). Blackwee Scientific Publications, Inc, Boston. pp. 377–384.
24. Nussbaum S R, Zahradnik R J, Lavigne J R et al. Highly sensitive two site immunoradiometric assay of a parathyrin and its clinical utility in evaluating patients with hypercalcemia. Clin Chem 1987;33:1364–1367.
25. Adams J S, Clemens T L, Holick M F. Silica sep-pak preparative chromotography for vitamin D and its metabolites. J Chromotogra 1981;226:198–201.
26. Reinhardt T A, Horst R L, Orf J W, Hollis B W. A microassay for 1,25 dihyroxyvitamin D not requiring high pressure liquid chromatography: applications in clinical studies. J Clin Endocrinol Metab. 1984;58:91–98.

What is claimed is:

1. A method of treating a subject afflicted with polycystic ovarian syndrome which comprises administering to the subject an amount of calcium or a derivative thereof effective to treat the polycystic ovarian syndrome.

2. A method of treating a subject afflicted with polycystic ovarian syndrome which comprises administering to the subject an amount of vitamin D or a derivative thereof effective to treat the polycystic ovarian syndrome.

3. A method of treating a subject afflicted with polycystic ovarian syndrome which comprises administering to the subject a combination of calcium or a derivative thereof and vitamin D or a derivative thereof in an amount effective to treat the polycystic ovarian syndrome.

4. The method of claim 2, wherein the vitamin D derivative is ergocalciferol (D2), cholecalciferol (D3), calcidiol (25 hydroxyvitamin D), or calcitriol (1,25 dihydroxyvitamin D).

5. The method of claim 3, wherein the vitamin D derivative is ergocalciferol (D2), cholecalciferol (D3), calcidiol (25 hydroxyvitamin D), or calcitriol (1,25 dihydroxyvitamin D).

6. The method of claim 1, wherein the calcium derivative is calcium carbonate, calcium citrate, calcium gluconate, calcium lactate, calcium acetate, or calcium stearate.

7. The method of claim 3, wherein the calcium derivative is calcium carbonate, calcium citrate, calcium gluconate, calcium lactate, calcium acetate, or calcium stearate.

8. The method of claim 1, wherein the amount of calcium administered is from about 500 to about 3000 mg per day and is administered orally.

9. The method of claim 6, wherein the calcium is calcium carbonate and the amount is from about 300 mg to about 400 mg and is administered orally two–six times per day.

10. The method of claim 4, wherein the vitamin D derivative is vitamin D2 or D3 in an amount from about 400 to about 5000 IU per day and is administered orally.

11. The method of claim 4, wherein the vitamin D derivative is vitamin D2 or D3 in an amount from about 50,000 to about 300,000 IU per week and is administered orally.

12. The method of claim 4, wherein the vitamin D derivative is vitamin D2 in an amount from 100,00 to about 500,000 IU and is administered intramuscularly in an oil base once every 2–3 months.

13. The method of claim 1, 2, or 3, wherein the administration is effected orally, sublingually, parenterally, or transdermally.

14. The method of claim 4, wherein the vitamin D derivative is calcitriol in an amount from about 0.25 to 1.00 mcg per day and is administered orally.

15. The method of claim 3, wherein the calcium or the derivative thereof is in an amount of about 1500 mg per day and the vitamin D or the derivative thereof is in an amount of about 2000 IU per day.

16. The method of claim 3, wherein the calcium or the derivative thereof is in an amount of about 1500 mg per day and the vitamin D or the derivative thereof is in an amount of about 3000 IU per day.

17. The method of claim 3, wherein the calcium or the derivative thereof is in an amount of about 1000 mg per day and the vitamin D or the derivative thereof is in an amount of about 2000 IU per day.

18. The method of claim 3, wherein the calcium or the derivative thereof is in an amount of about 1000 mg per day and the vitamin D and the derivative thereof is in an amount of about 1000 IU per day.

19. The method of claim 3, wherein the calcium or the derivative thereof is in an amount of about 500 mg and the vitamin D or the derivative thereof is in an amount of 800 IU.

20. The method of claim 19, wherein the administration is twice or three times per day.

21. The method of claim 3, wherein the calcium or the derivative thereof and vitamin D or the derivative thereof are administered in the form of a tablet, capsule, powder, liquid, candy, cookie, or transdermal patch.

* * * * *